United States Patent [19]
Sedivy

[11] Patent Number: 5,851,408
[45] Date of Patent: Dec. 22, 1998

[54] ELIMINATION AND INHIBITION OF BIVALVE MOLLUSK ATTACHMENTS

[76] Inventor: John Joseph Sedivy, 167 Concord Meeting, Glen Mills, Delaware County, Pa. 19342

[21] Appl. No.: 789,365

[22] Filed: Jan. 24, 1997

Related U.S. Application Data

[60] Provisional application Nos. 60/011,485, Feb. 12, 1996 and 60/030,921, Nov. 14, 1996.

[51] Int. Cl.⁶ ........................................... C02F 1/68
[52] U.S. Cl. ............................................ 210/764; 514/579
[58] Field of Search ..................... 210/749, 764, 210/696; 514/579

[56] References Cited

U.S. PATENT DOCUMENTS

| | | |
|---|---|---|
| 3,207,593 | 9/1965 | Lindaberry . |
| 4,816,163 | 3/1989 | Lyons et al. . |
| 4,857,209 | 8/1989 | Lyons et al. . |
| 4,906,385 | 3/1990 | Lyons et al. . |
| 4,970,239 | 11/1990 | Whitekettle et al. . |
| 5,015,395 | 5/1991 | Muia et al. . |
| 5,062,967 | 11/1991 | Muia et al. . |
| 5,096,601 | 3/1992 | Muia et al. . |
| 5,128,050 | 7/1992 | Gill et al. . |
| 5,236,493 | 8/1993 | Hunter et al. ............................. 106/16 |
| 5,290,805 | 3/1994 | Eastman et al. . |
| 5,380,762 | 1/1995 | Morgan ................................... 514/673 |
| 5,413,722 | 5/1995 | Eastman et al. . |
| 5,565,021 | 10/1996 | Vanlaer ..................................... 106/18 |
| 5,622,995 | 4/1997 | Fellers et al. ........................... 210/764 |

FOREIGN PATENT DOCUMENTS 1.460.037  10/1966  France .

OTHER PUBLICATIONS

Public Health Report, vol. 82, No. 9, Sep. 1967, Seiffer and Schoof.

*Primary Examiner*—Jay H. Woo
*Assistant Examiner*—Betsey J. Morrison
*Attorney, Agent, or Firm*—Stanley A. Marcus; Gilbert W. Rudman

[57] ABSTRACT

A process is disclosed for the eradication of and subsequent inhibition of bivalve mollusk settlement on solid surfaces immersed in water inhabited by said mollusk comprising introducing into said water, a specified tertiary amine salt at a rate and for a time at least sufficient to inhibit settlement of said mollusk.

19 Claims, No Drawings

ELIMINATION AND INHIBITION OF BIVALVE MOLLUSK ATTACHMENTS

BACKGROUND OF THE INVENTION

This Application claims the benefit of United States Provisional Applications 60/011,485 filed Feb. 12, 1996 and 60/030,921 filed Nov. 14, 1996.

This invention is a process for the eradication and inhibition of bivalve mollusk attachments to solid surfaces immersed in water inhabited thereby. More particularly, the process involves the introduction into water inhabited by bivalve mollusks, in various stages of development, of a specific tertiary amine salt in an amount at least sufficient to inhibit settlement of the mollusks to any proximate solid surface.

One form of bivalve mollusks, Zebra mussels, are believed to have been first delivered to North America from Europe in the ballast of a ship. On discharge of the ballast in Canadian waters, colonies of these mussels quickly developed and spread through the Great Lakes and surrounding rivers and lakes.

Zebra mussels, in both the mature and larval (veliger) stages, cause serious fouling or obstruction problems by attachment to subsurface solids and then to the shells of each other to build clumps of the mollusks across openings in conduits, e.g., cooling water intake and effluent pipes of industrial and electrical generating plants, and intakes of water supply facilities. Additionally, the mollusks excessively weight stress or foul tank and cooling tower walls, underwater equipment, ship bottoms and ballast compartments, oil rigs, locks, docks, pilings, dams, linings of canals, anchors, gratings, valves and various other subsurface structures and equipment in water infested with these organisms.

For the purpose of this invention, the term bivalve mollusks includes Zebra mussels (Dreissena polymorpha) and other bivalve mollusks having larval (veliger) stages which are free to swim and attach to (settle on) solid surfaces, e.g., Blue mussels, Quagga mussels (*Dreissena bugenis*) and Asiatic clams (*Carbicula fluminea*). Zebra and Quagga mussels have fibrous tentacles called byssal threads which enable firm attachment to underwater solid surfaces.

PRIOR ART

There are various prior publications disclosing the chemical treatment of water inhabited by mollusks to prevent settlement on or to effect detachment of the mollusks from solid subsurfaces. Some of these prior references are directed to quaternary ammonium salts and polymers thereof, and mixtures of the salts and polymers, e.g., U.S. Pat. Nos. 4,857,209; 5,015,395; 5,062,967; 5,096,601; and 5,290,805. Other prior publications teach the use of water soluble $C_8$–$C_{18}$ alkyl guanidine salts to control mollusk fouling, e.g., U.S. Pat. No. 4,816,163. A literature reference, Public Health Report, Vol. 82, No. 9, 9/67, pp. 833–9, "Tests of 15 Experimental Molluscicides Against Australorbis Glabratus" teaches that both the mono and di (N,N-dimethyltridecylamine) salts of Endothall are effective at 10 and 5 ppm respectively to kill Puerto Rican snails. Chlorine, generated, for example, by the introduction of chlorine gas or sodium hypochlorite into the infested water, has been the prevalent control agent for mollusks. While the known chemical treatments for the control of Zebra mussels are generally effective, their use can result in undesirable environmental consequences, particularly with respect to persistence and toxicity to nontarget organisms.

Tertiary amine salts of 3,6 endoxohydroorthophthalic acid are disclosed in U.S. Pat. No. 3,207,593, issued Sep. 21, 1965, as effective for the control of submersed aquatic plant life.

STATEMENT OF THE INVENTION

This invention is a method for the control of bivalve mollusks to effect detachment from and inhibit settlement on a solid immersed in water inhabited by said mollusks comprising introducing into said water a tertiary amine salt of an inorganic or organic acid, the amine radicals of said salt derived from an amine having the formula:

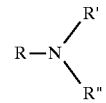

where R is an aliphatic hydrocarbon group containing from about 6 to about 20 carbon atoms and R' and R" are the same or different alkyl radicals having from 1 to about 20 carbon atoms, and mixtures of said amine radicals, said amine salt being introduced at a rate and for a length of time sufficient to at least inhibit settlement of the larva stage of mollusks on said solid.

This invention also includes a method comprising first eradicating, by any means, bivalve mollusk attachments to a solid immersed in water. Preferably, a tertiary amine salt as defined above is introduced into the mollusk infested water at a rate and for a time sufficient to cause detachment of said mollusk attachments. Then, introducing into said water the above-described tertiary amine salt but at a rate at least sufficient to inhibit the settlement of larva stage bivalve mollusks to said solid.

DETAILED DESCRIPTION OF THE INVENTION

Bivalve mollusks in various stages of maturity are eradicated in accordance with this invention by exposure for a period of time to tertiary amine salts wherein the amine radical is derived from an amine of the following formula:

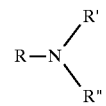

where R is an aliphatic hydrocarbon group containing from about 1 to about 20 carbon atoms and R' and R" are the same or different alkyl radicals having from 1 to about 20, preferably from 1 to 8 carbon atoms. Examples of these alkyl radicals include methyl, ethyl, propyl, butyl, hexyl, octyl, decyl, dodecyl, octadecyl, eicosyl, and isomers thereof. The aliphatic hydrocarbons represented by R include, for example, the $C_1$–$C_{20}$ alkyl radicals described above for R' and R" as well as those groups on amines obtained by reductive amination of the acids from animal fats and vegetable oils, particularly tallow and coconut acids which have predominantly 12 to 18 carbon atoms in the chains. Of particular value for this invention are coconut oil amines (predominantly twelve and 14 carbon atoms) which have been converted to tertiary amines by alkylation. However, other tertiary amines within the above structural configuration are also operable in this invention and such amines may be obtained by the amination and subsequent alkylation of, e.g., caproleic, oleic, linoleic, tallow, and soya acids. Alternatively, these tertiary amines may be obtained by conversion of the acids to an amide with a di-lower alkyl secondary amine followed by reduction of the carbonyl group. Specific amines which are preferably used to form the salts useful in this invention include N,N-dimethylcaprylamine, N,N-dimethyllaurylamine, N,N-diethylmyristylamine, N,N-dipropylstearylamine and the like. However, because of availability and cost, mixtures of amines are most preferably used such as the mixtures found in N,N-dimethylcocoalkylamines, N,N-dimethylsoyaamine, synthetic fatty acid amines, and the like. The methods of making these amines are well known, the various processes being disclosed in the text by Astle entitled Industrial Organic Nitrogen Compounds (Reinhold, 1961).

The tertiary amine salts of this invention contain amine radicals as previously described while the acid or anhydride useful for the formation of the salt with the tertiary amine may be any inorganic or organic acid or anhydride thereof which does not appreciably decrease the activity of the tertiary amine moiety. The inorganic acids will include, for example, compounds of the formula HX where X equals chlorine, bromine, iodine, —NO$_3$, —HSO$_4$, —H$_2$PO$_4$ and the like. The organic acids will include, for example, di- or polybasic carboxylic acids containing 1 to 24 carbon atoms, e.g., 3,6-endoxohydrophthalic acids and its anhydride (see U.S. Pat. No. 2,576,082).

A tertiary amine salt of preference is the inorganic acid salt of mono- or di- N,N-dimethylcocoamine, based on cost and commercial availability, or the inorganic acid salt of a synthesized chemical equivalent thereof.

The 3,6-endoxohydroorthophthalic acid salts of this invention will have less than three double bonds in the endoxocarboxylic acid ring, but may have all three degrees of ring saturation and thus will include 3,6-endoxodihydroorthophthalic acids, (e.g.

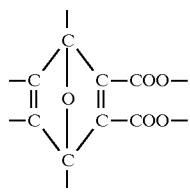

3,6-endoxotetrahydroorthophthalic acids, (e.g.

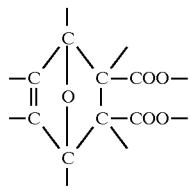

and

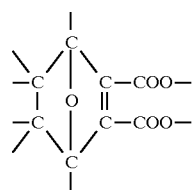

and 3,6-endoxohexahydroorthophthalic acids (e.g.

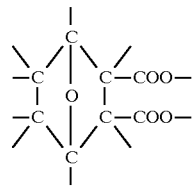

In this group, the latter compounds (i.e., the hexahydro compounds or endothalls) are the preferred anions to be used.

Where anhydrides are used, a mole of water is required, of course, to cause hydrolysis to the dibasic acid. In addition to the unsubstituted acids, monovalent radical substituted derivatives may be used and such substituents will include halogens (e.g., chlorine, bromine, etc.), lower alkyl, lower alkoxy, lower aryl, lower aryloxy, nitro, cyano, haloalkyl (e.g., trifluoromethyl) and like groups. The substituted acids from which the salts useful in this invention are derived, are described and their preparation given in U.S. Pat. No. 2,576,080.

Examples of the techniques which may be used to prepare these salts are disclosed in U.S. 2,576,082.

The compounds used in this invention when made from commercial amines are generally clear or slightly turbid tan or brown oils or syrups which do not readily lend themselves to crystallization. This resistance to crystallization is probably due to the fact that the commercial amines used to form the salts are comprised of more than one discrete amine species and such a mixture makes crystallization impossible. However, this is not important because the amine salt oil obtained as product is simply dissolved in a suitable solvent for use. When individual specific amines are used for salt formation, however, the products are waxy or soap-like solids. The products used in this invention are readily soluble in water, ethanol and other alcohols, benzene, toluene, xylene and other aromatic hydrocarbons, diethyl ether, diacetone alcohol, etc.

The active tertiary amine salt is usually used in the process of this invention as a water-based formulation containing, for example, from 25 to 75 weight percent of the active salt. Other ingredients may also be incorporated in the formulation including effective amounts of one or more dispersants, for example, isopropyl alcohol, diacetone alcohol, other water soluble alcohols and/or ketones, up to about 40 weight percent of the formulation. Surfactants for improving the dispersibility or suspensibility of active agents in water may be included in the formulation. Anionic and/or nonionic surface active agents may be employed including, for example, sodium lauryl sulfate, sodium alkylbenzene-sulfonate, sodium sulfosuccinate, sodium salt of ligninsulfonic acid, polyvinylpyrolidone and its water-soluble alkylated derivatives, polyoxyethylene fatty alcohol ethers and other well-known surfactants. Antifoam agents, e.g., ecologically safe defoamers meeting federal regulations, may be included. Various inert carriers or diluents are useful for the formulations including water-soluble or dispersible solids, e.g., sucrose, soluble starches, sugars, absorbent graft copolymers of polyhydroxy polymers, acrylonitrile and acrylic comonomers. Other adjuvants well known in the agricultural formulation field may also be used in the formulation of this invention to improve or hasten the effectiveness of bivalve mollusk control in the process of this invention.

It is further contemplated that other molluscicides and aquatic pesticides may be incorporated in the formulations containing the amine salts used for bivalve mollusk control and control of other aquatic pests.

Granular formulations may be prepared using the active tertiary amine of this invention along with the usual adjuvants and carriers, i.e., clays and surfactants.

The toxicity of the amine salt of this invention to bivalve mollusks is dependent on the rate of application and the time period of exposure. Exposure of attached bivalve mollusks under static conditions to from more than 0.5 up to about 10.0 parts per million (ppm) of the active amine salt for a time period of from about 1 to 24 hours (the lower the concentration, the longer the time) will serve to release or cause detachment of substantial amounts of bivalve mollusks from the solid to which they are attached, generally by lethal reaction. Preferably, a rate of about 1.5 to 3 ppm over about 4 to about 8 hours, more preferably, a rate of about 1.5 to 2 ppm for about 6 to 8 hours, is applied to effect clean out of the mollusk fouled zone. Under dynamic conditions, for example, when a discharge or intake pipe is obstructed with clumps of bivalve mollusks, the amine salt is incorporated into the moving or running water at a rate which will substantially continuously subject the mollusks to exposure to the toxic amine salt in the amounts stated for the static conditions and for the same length of time. That is, sufficient active agent is dripped, pumped or otherwise injected into the flowing water of the water-way to be treated to produce a substantially continuous concentration of the agent, proximate the attached mollusks of over 0.5 up to about 10.0 ppm for from 1 to 20 hours, preferably about 1.5 to 3 ppm for 4 to 8 hours, more preferably about 1.5 to 2 ppm for 6 to 8 hours. On completion of this treatment, a substantial amount of the mollusks will have detached by release of their attachment means from the solid surface to which they were attached, and, if the water flow rate is sufficient and unrestricted, will have washed away.

After clean out or removal of the obstructing or fouling mollusks, the area may be maintained in substantially clean condition by a maintenance dosage procedure involving the introduction of the molluscicide into the channel, conduit or other confined waterway, or into a large body of water at least proximate the solid surface sought to be maintained free of attachment of veligers, juveniles and mature bivalve mollusks, at a rate and time sequence effective to accomplish this. A rate of introduction of about 0.2 to about 1 ppm continuously over from about 1 to 4 hours, and then the dose repeated every 8 to 16 hours. Preferably, this dosage procedure is for from about 0.4 to about 0.6 ppm continuously for 1.5 to about 2.5 hours repeated every 10 to 14 hours. Of course, these prescribed rates and times relate to the degree of toxicity of the active molluscicide. For example, if one employs a ditertiary amine salt rather than the more active monotertiary amine salt, reduced amounts and shorter times will be applicable and these are to be determined empirically for each amine salt disclosed by referencing the amounts prescribed for the preferred compound.

While the preferred method for maintaining an underwater free of bivalve mollusks in an infested area is to use the clean-out process of this invention by introducing into the water to flow proximate to a solid to which the mollusks are attached, an effective amount of the prescribed tertiary amine salt at a rate and length of time sufficient to cause detachment of the mussels. For freeing underwater solid surfaces from mollusk attachment, other chemical, physical and mechanical, or combinations of these treatments, may be used for first eradicating the mollusks prior to using the prescribed maintenance dosage program for maintaining an area free of bivalve mollusk settlement. Mechanical scrapers and reamers may be used to clean the mollusks from the subsurface to which they are attached. Heat treatment of the underwater solids at temperatures in excess of 35° C. for several hours is lethal to mollusks of the Zebra mussel variety. Shock generated by an electrical charge in the infested area, while expensive, will detach the mollusks and veligers from an underwater solid.

An advantage for the amine salt of this invention is that, particularly for concentrations below about 0.5 ppm, it does not require a holding period or deactivation after use. It does not hydrolyze or photolyze in an aqueous environment. Additionally, the tertiary amine, at the prescribed treatment concentration, cleans scale, slime, algae and other deposits from intake and outlet conduits through which it passes.

There are at least three areas which can be compared that clearly set the amine salt of this invention, apart from commercially used quaternary ammonium compounds, i.e., quats. These are explained in the following numbered paragraphs 1–3.

1. Aquatic Species Toxicity

LC50/EC50 values are the concentration of a material required to cause 50% mortality in a test population. The numbers below were taken from 96-hour flow through studies which is the standard test required by EPA. This means that the test material* was injected as a flow through (constant level of exposure) treatment for a period of 96 hours. It is believed that this type of testing produces biased (less favorable) results for the amine salt because the half life of the amine salt is considerably less than 96 hours and the species exposed are subject to one short exposure followed by rapid dissipation, not a constant level of exposure. It is not expected that there will be much difference in the toxicity level of the quats when comparing 24- and 96-hour exposures.

Results of 96-hour flow through aquatic studies LC50/EC50 values expressed as mg/l:

| Test species | TD Amine Salt* | Quat |
| --- | --- | --- |
| Daphnid | .32 | .02 |
| Shrimp | 2.4 | .08 |
| Minnow | 3.5 | .36 |
| Bluegill | 1.7 | .88 |
| Traut | 1.0 | 1.0 |

\* -monon-tertiary-dimethylcocoamine salt of endothall

Differences vary from a factor of 30 to 1 for the Daphnid and Shrimp down to 2 to 1 for the Bluegill. The difference of 0 for the Trout is believed to be an aberration.

2. Aquatic Half Life

From biological observations, the half life of the preferred amine salt of this invention is in the 24-hour range. The half life of a commercially used quat, available as CP-4 and CT-2 (Clam-trol®) composed of three cationic surfactants (N-alkyl dimethyl-benzyl ammonium chloride), is believed to be 28 days (Technical Session—International Zebra Mussel Conference in Toronto, Canada, 1995). The half life difference between the amine salt of this invention and CP-4 is 28 fold.

3. Release Rates of Zebra Mussels

Plant operators who have used the amine salt of this invention in an experimental program, e.g., as reported in the following examples, and who have used quats in commercial applications to eliminate Zebra mussel attachments from plant water systems, indicate that release of the mollusks with the use of quats is from 24 to 48 hours after treatment while they consistently report an 8 to 12 hour release period for the mollusks after treatment with the amine salt of this invention.

The plant effluent containing the quats must be expensively treated for decontamination by passing it through beds of bentonite clay to deactivate before discharge.

The process of this invention is most effective in waters in the temperature range of about 18° C. up to about 25° C., preferably 20°–22° C. for the control of Zebra mussel.

The following examples are set forth to demonstrate the effectiveness of the present invention.

EXAMPLE 1

A synthetic tertiary, mixed $C_8$–$C_{20}$ alkyldimethyl amine* salt of hydrochloric acid, at a formulation concentrating of above 53% by weight, was tested for its effectiveness for the elimination of Zebra mussels by an independent university laboratory experienced in the testing of molluscicides. The toxicity of the above described amine salt to Dreissena polymorpha (Zebra mussels) was tested using both the Spearman-Karber (S-K) method and the Litchfield-Wilcoxon (L-W) method, both at 17° C. The results of the tests, which report lethal concentration (LC50) for large and small mussels, are set forth in the following Table 1.

*ADMA™ WC Alkyledimethylamine for Albemarle Corporation

TABLE 1

|  | S-K Method | L-W Method |
|---|---|---|
| MUSSEL SHELL LENGTH, 5–8 mm | | |
| 24 hours - LC50*, ppm | 1.17 (0.89–1.55)** | 1.44 (1.06–1.96) |
| 48 hours - LC50, ppm | 0.44 (0.32–0.59) | 0.51 (0.33–0.78) |
| MUSSEL SHELL LENGTH, 20–25 mm | | |
| 24 hours - LC50, ppm | 2.03 (1.67–2.46) | 2.0 (1.45–2.75) |
| 48 hours - LC50, ppm | 1.37 (1.19–1.57) | 1.35 (1.16–1.58) |

* - Concentration of molluscicides which is lethal to 50% of the test species in period of test time.
** - Range in brackets is the 95% confidence limits of lethal ppm.

Additional experiments were conducted by the same independent laboratory referred to above in which Zebra mussels were exposed to a single concentration of the hydrochloric acid amine salt for varying periods of time to determine toxicity results (lethal times) for large and small mussels.

The data developed are summarized in Tables 2 and 3 below.

TABLE 2

| Amine Salt Conc., ppm | Mortality % Time (hours) | | | | | | |
|---|---|---|---|---|---|---|---|
| | 6 | 24 | 30 | 48 | 72 | 96 | 120 |
| Mussel shell length, 0.5–0.8 cm | | | | | | | |
| 0 | 0 | 0 | 0 | 0 | 0 | 0 | 0 |
| 0.25 | 0 | 0 | 0 | 0 | 2 | 4 | 14 |
| 0.50 | 6 | 12 | 20 | 36 | 50 | 62 | 66 |
| 1.00 | 6 | 76 | 82 | 96 | 100 | | |
| Mussel shell length, 2.0–2.5 cm | | | | | | | |
| 0 | 0 | 0 | 0 | 0 | 0 | 0 | 13 |
| 0.25 | 0 | 0 | 0 | 0 | 2 | 4 | 6 |
| 0.50 | 0 | 0 | 2 | 4 | 10 | 20 | 32 |
| 1.00 | 4 | 32 | 38 | 80 | 100 | | |

Chemical solutions were renewed every 24 hours (5 replicates, 10 mussels per replicate)

The mean lethal time (LT50) of the hydrochlorine acid salt of tertiary $C_8$–$C_{20}$ alkyldimethylamine to Zebra mussels of the different sizes was tested in accordance with the method of Litchfield and Wilcoxon (1949) by the independent research laboratory producing the results of Table 3 below.

TABLE 3

| Mussel shell length | t-amine salt conc. | LT50 (hr) | 95% Confidence limits |
|---|---|---|---|
| 0.5–0.8 cm | 0.5 | 72 | 60–87 |
| 0.5–0.8 cm | 1.0 | 15.5 | 12–20 |
| 2.0–2.5 cm | 1.0 | 33 | 30–37 |

Independent Testing Laboratory Comments: It was not possible to estimate an LT50 for each exposure concentration because, in several cases, mortality was either too high or too low. However, at an exposure concentration of 1.0 ppm, LT50's of 33 hours and 15.5 hours were estimated for large and small mussels, respectively, as shown in Table 3. Furthermore, an LT50 of 72 hours was estimated for small mussels at an exposure concentration of 0.5 ppm. Thus, it should take exposure times of 72 hours to result in 100% mortality of both large and small mussels at an exposure concentration of 1.0 ppm.

Based on a battery of 30 or so chemicals tested by the independent testing laboratory, it observed that the hydrochlorine acid salt of the tertiary $c_8$–$C_{20}$ as chlorine and substantially more toxic to Zebra mussels than certain other molluscicdes which are commercially available, e.g., Clam-Trol® CT1 and Calgon® H-130.

EXAMPLE 2

A field efficacy study was conducted to evaluate the appropriate concentration of mono(N,N-dimethylcocoamine) salt of endothall (3,6-endoxohexahydroorthophthalic acid) (HYDROTHOL® 191—a.i. 53 wt. %) required to control Zebra mussels in the Cleveland Electric Eastlake Power Plant on Lake Erie.

Clumps of viable Zebra mussels were added to each of four (4) bioboxes, which had inside dimensions of 16-¾× 10-¾×9 inches, constructed of plexiglass and silicone adhesive with a 2-½ inches high water intake tube. The water depth was maintained at 7-½ inches by a 7-½ inches high drain. Two (2) of these bioboxes were connected into the house service water system and two (2) bioboxes were connected into the low pressure service water system of the plant. Injection points for a formulation of the above-identified endothall salt (53% active ingredient) were located on the suction side of the eight (8) house service water pumps used in the system. The injection pumps were calibrated to deliver an endothall salt concentration of 2 ppm. The low pressure service water system was not treated, the two bioboxes attached to this part of the system serving as untreated controls.

At six (6) hours after injection began, mussels within the treated bioboxes appeared to be gapped open, not filtering and nonresponsive. After eight hours, the treated bioboxes installed in the house service system were opened and Zebra mussels were removed for further evaluation. All mussels from the treated bioboxes were considered nonviable. Mussels from the untreated bioboxes installed in the low pressure service system appeared normal, showed active filtering and responded to gentle probing.

Analytical results showed an average concentration of endothall salt in the first treated biobox of 0.70 ppm and in the second treated biobox of 1.72 ppm over the eight hour treatment period. Based on the analytical results of the filter house samples of the power plant system during the test, the overall concentration of endothall salt in the plant discharge channel was calculated to be 0.014 ppm.

The effective concentration of endothall salt for the control of Zebra mussels in the above test during a 6 to 8 hour treatment period is 1.0 to 1.5 ppm.

EXAMPLE 3

Another field efficacy study with the mono(N,N-dimethylcocoamine) salt of endothall (as in Example 2) was conducted at the Toledo Edison Bay Shore Station, which is about five miles east of downtown Toledo, Ohio, at the western end of Lake Erie at the mouth of the Maumee River.

Clumps of viable Zebra mussels were added to each of three bioboxes, as described in Example 2, that were connected to the water flow pipes at separate sites within the power plant. The bioboxes were equilibrated for several days prior to the initiation of study. Injection points for the endothall salt formulation (53% active) were located on the suction side of the raw water pumps and on a service water header. The injection pumps were calibrated to deliver a constant endothall salt concentration of 3 ppm. The study was planned for a 48 hour exposure.

Water samples were taken from the bioboxes, the cooling water tank and two (2) Maumee River effluent sites. Concentrations of the endothall salt were analytically measured for each of these sites at various intervals by taking samples from the first four mentioned sites at 0, 1, 2, 4 and 8 hours while samples were taken from the two Maumee River effluent sites at 0, 4, 8, 12, 16, 24, 28, 32 and 36 hours. Additionally, water samples were taken from the second Maumee River site at 44, 52, 60, 68, 76 and 84 hours.

At 1, 2 and 4 hours after initiation of the treatment, the Zebra mussels in the bioboxes appeared viable. At the 8 hour interval, all mussels within bioboxes 1, 2 and 3 were gapped open and nonresponsive to external stimuli. The bioboxes were opened and the mussels removed for further evaluation. All mussels from biobox 2 were considered nonviable while other mussels showed slow response and were not expected to survive.

Static bioassays were conducted on the samples taken from the Maumee River sites. These tests were standard 48 hour Daphnia magna and 96 hour fathead minnow studies as specified under the U.S. Environmental Protection Agency. The tests were conducted with 100% effluents. None of the bioassay samples was acutely toxic to Ceriodaphnid or fathead minnows.

EXAMPLE 4

Still another field study was performed to determine the efficacy of low-level intermittent treatments of mono(N,N-dimethylcocoamine) salt of endothall to inhibit primary and secondary settlement of Zebra mussels under field conditions.

The study was conducted at Ontario Hydro's Zebra Mussel Research Facility on Lake Erie at Nanticoke, Ontario. This site has large numbers of veligers and translocating juveniles (larva stages of mussels). Tests were performed in 16 continuous flow through cells (91 cm length×13 cm diameter) with nominal residence times of 30 minutes to simulate worst-case settlement conditions in generating station service water systems. Triplicate treatments consisted of controls and intermittent dosing of the cells with a formulation of the endothall salt (53% active—available as HYDROTHOL® 191 Aquatic Algicide and Herbicide from Elf Atochem North America, Inc.) at a target level of 0.5 ppm (mg/L-active ingredient) continuously for 2 hours and a repetition every 12 hours to provide increasing daily intermittent dosages of 0, 2, 4, 6 and 8 ppm. Over the 10-week treatment period, measured endothall salt concentrations were within 20% of the target amount. Inlet lake water temperatures ranged from 18° to 27° C., the average veliger density was 2130 per cubic centimeter and the average flow rate through the test cells was 0.73 L/min.

Compared to untreated controls, the various treated cells demonstrated a 71 to 100% reduction in the numbers of live mussels attached to flow cell surfaces after a 10-week treatment period. One-way analysis of variance (ANOVA) indicated that this difference was significant. Further analysis using the LSD multiple range test at the 95% confidence level showed that each of the treatments (2, 4, 6 and 8 ppm/hour) had resulted in significantly fewer numbers of attached live mussels than the untreated control and that different intermittent doses had similar efficacy. Most live Quagga mussels were less than 2.5 mm. in length indicating likely attachment within the 2 to 3 weeks prior to trail completion. Translocating mussels were not evident in the treated cells. The unexpectedly low degree of settlement in control cells, 43 per square meter, accompanied by normally high natural mortality may have contributed to the inability to distinguish between treatments of increasing intermittent dosage. When the present data was compared to a previous trial carried out at daily intermittent dosages ranging from 0.5 to 2 ppm/hour, a minimum value of about 2 ppm/h. (0.5 mg/L for 2 hours every 6 hours) is suggested for efficacious control of mussels.

EXAMPLE 5

A comparative study of the efficacy of several molluscicides including those meeting the description of those claimed herein was performed by a commercial, independent testing laboratory having expertise in this field. The purpose of these test was to compare LT50's and the times-to-an-effective-kill (80–90%) of the Zebra mussel exposed to the test molluscicides currently being used commercially, and several experimental materials, for a total of eight (8) tests. Twenty-four hour static exposure here conducted with adult Zebra mussels (approximately 10–20 minutes). The physical system and procedure used in carrying out the tests is described below:

The test chambers were 90×50 mm glass crystallizing dishes containing 200 mL of test solution. Three replicates of 10 Zebra mussels each were maintained for each exposure concentration and control. Mussels were added impartially by introducing the mussels, two at a time, to each dish until all dishes contained 10 mussels.

Dilution water was unadulterated water from a 100 meter bedrock well supplemented on demand with untreated town well water characterized as soft water with a typical total hardness of 20–40 mg/L as $CaCo_3$ and an alkalinity of 20–35 mg/L $CaCo_3$. The pH range is from 6.9 to 7.5 and the specific conductance range is 80–150 micromhos/cm. These parameters were monitored weekly to assure that they remained in the typical ranges. Total hardness and alkalinity were determined according to Standard Methods for the Examination of Water and Wastewater (APHA, 1989). Periodic analysis of representative samples were conducted to assure the absence of substances harmful to aquatic organisms.

The water temperature of the test solutions was maintained at approximately 20° C. by ambient laboratory (controlled) temperature. The photoperiod was maintained at 16 hours light, 8 hours darkness using an automatic timer. Total dissolved oxygen concentration was >80% of saturation during the tests. The Zebra mussels were placed into the exposure solutions within 30 minutes of their preparation.

At test initiation, duplicate water samples of an appropriate volume were taken from each concentration and control solution (before distribution to the exposure vessels) for determination of test material concentration. Ion chromatography was used to analyze Endothall (Tests #1–#3). Ampermatic titration was used for chlorine (Test #4). Spectrophotometric methods were used for poly DMDAAC (polyquat) and Clam-Trol® (Tests #5 and #6) and GC-NPD method was used for the amines (Tests #7 and #8). All samples were taken from a point approximately midway between the surface, bottom and sides of each test vessel.

Biological observations were made for mortality and sublethal effects (e.g., closed or gaped shells). Mortalities were recorded and removed when observed.

LT50 results were determined by observations made and recorded at 0,2,4,6,8,10,12,16,20 and 24 hours post-treatment. Mortality data derived from the tests were used to statistically estimate at median lethal time (LT50) and the 95% confidence interval for each concentration of each material tested. The LT50 is the time (hours) which produces 50% mortality in the tests organism population at the stated test material concentration. A computer program used to calculate LC50 (lethal concentration to produce 50% mortality in the test organism) values was used to calculate the LT50 values.

The results are summarized in the following table.

TABLE 5

| Active Test Material | Measured Concentration (mg/L) | LT50 (hrs.) |
| --- | --- | --- |
| 1. Cocoamine-Endothall salt of Example 2 (5 ppm acid eqv.) | 6.5 | 6.0 |
| 2. Cocoamine HCl salt (5 ppm acid equiv.) | 9.9 | 5.8 |
| 3. Synthetic mixed t- $C_8$–$C_{20}$ Alkyldimethylamine-Endothall salt (5 ppm acid eqv.) | 7.4 4.5 | 5.5 10.9 |

TABLE 5-continued

| Active Test Material | Measured Concentration (mg/L) | LT50 (hrs.) |
| --- | --- | --- |
| 4. Synthetic mixed t-$C_2$–$C_{20}$ alklyldimethylamine - HCl salt of Example 1 (5 ppm acid eqv.) | 11 | 5.2 |
| 5. Dipotassium Salt of Endothall (AQUATHOL ®k) | 460 250 | 8.5 13.0 |
| 6. Clam-Trol ® CT-2 (Betz Labs) (N-alkyl dimethylbenzyl ammonium chloride) | 6.6 4.0 | 13.0 >24.0 |
| 7. Polyquat (Calgon Corporation) [poly (dimethyldiallyl ammonium chloride)] | 8.3 | >24.0 |
| 8. Chlorine | 2.5 | >24.0 |

The nominal concentrations of the Endothall salts were intended to be 5 ppm as Endothall acid. The amine-hydrochloride salt concentrations were calculated to be the equivalent amount of amine at 5 ppm Endothall acid in the amine-Endothall salt. Clam-Trol® and Polyquat concentrations are based on total product. It is apparent from the above-reported static tests that the t-amine salts of the present invention are significantly effective against Zebra mussel infestation and substantial more effective than commercial molluscicides particularly at lower dosage.

I claim:

1. A method for the control of bivalve mollusks to effect detachment from and to inhibit settlement on solids immersed in water inhabited by said mollusks comprising introducing into said water an amine salt of an inorganic or organic acid, the amine radical of said salt derived from an amine having the formula:

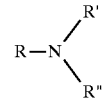

where R is an aliphatic hydrocarbon group containing from about 8 to about 20 carbon atoms and R' and R" are the same or different alkyl radicals having from 1 to about 8 carbon atoms, and mixtures of said amine radicals, said amine salt being introduced at a rate and length of time to at least inhibit settlement of the larva stage of said mollusk.

2. The method of claim 1 wherein said inorganic acid has the formula HX where X is chlorine, bromine, iodine, —$HSO_4$, —$NO_3$ or —$H_2PO_4$.

3. The method of claim 1 wherein said acid is a mono- or polybasic carboxylic acid containing from 1 to 24 carbon atoms.

4. The method of claim 1 wherein said rate ranges from about 0.25 to about 4 ppm and said length of time is from about 1 to 16 hours.

5. The method of claim 1 wherein said amine salt is the monoamine salt.

6. The method of claim 1 wherein said amine salt is the diamine salt.

7. The method of claim 5 wherein said rate ranges from about 1 to 4 ppm and the length of time is from about 6 to about 8 hours.

8. The method of claim 1 wherein said rate ranges from about 0.25 to about 1 ppm and said length of time is from about 1 to 3 hours and this dosage is repeated every 8 to 16 hours.

9. The method of claim 1 wherein R is cocoamine, R' and R" are each methyl and the amine salt is a monoamine salt.

10. The method of claim 9 wherein said rate is about 1.5 to about 2 ppm for a length of time of about 6 to 8 hours.

11. A method for the continuous control of bivalve mollusks to effect detachment from and inhibit settlement on a solid immersed in water inhabited by said mollusks comprising the steps of (a) removing bivalve mollusk attachments from said solid by any means, and (b) thereafter introducing into said water an amine salt of an acid, the amine radical of said salt derived from an amine having the formula:

where R is an aliphatic hydrocarbon group containing from about 8 to about 20 carbon atoms and R' and R" are the same or different alkyl radicals having from 1 to about 8 carbon atoms, and mixtures of said amine radicals, the introduction of said amine salt being at a rate and for a length of time at least sufficient to inhibit the settlement of larva stage mollusks on said solid.

12. The method of claim 11 wherein said acid has the general formula HX where X is chlorine, bromine, iodine, —$HSO_4$, —$NO_3$ or—$H_2PO_4$.

13. The method of claim 11 wherein said acid is a mono- or polybasic carboxylic acid containing 1 to 24 carbon atoms.

14. The method of claim 11 wherein step (a) is accomplished by the introduction into said water of the amine salt introduced in step (b) but at a dosage rate and length of time at least sufficient to cause the attached mollusks to detach.

15. The method of claim 11 wherein said acid is 3,6-endoxohydroorthophthalic acid.

16. The method of claim 15 wherein R is cocoamine, R' and R" are each methyl and said amine salt is a monoamine salt.

17. The method of claim 16 wherein step (a) is accomplished by the introduction into said water of the amine salt introduced in step (b) but at a dosage rate and length of time at least sufficient to cause said attached mollusks to detach.

18. The method of claim 11 wherein said rate is from about 0.25 to about 1 ppm, said length of time ranges from about 1 to 3 hours, and the dosage is repeated every 8 to 16 hours.

19. The method of claim 16 wherein the dosage rate is about 1 to 4 ppm and said length of time is from about 6 to about 8 hours.

* * * * *